US00PP16226P3

(12) United States Plant Patent

Kanaya et al.

(10) Patent No.: US PP16,226 P3
(45) Date of Patent: Jan. 31, 2006

(54) *CALIBRACHOA* PLANT NAMED 'SUNBELPISUPU'

(50) Latin Name: ***Calibrachoa* sp.**
Varietal Denomination: Sunbelpisupu

(75) Inventors: Takeshi Kanaya, Omihachiman (JP); Yasuyuki Murakami, Gamo-gun (JP)

(73) Assignee: Suntory Flowers Limited, Tokyo (JP)

( * ) Notice: Subject to any disclaimer, the term of this patent is extended or adjusted under 35 U.S.C. 154(b) by 87 days.

(21) Appl. No.: 10/812,863

(22) Filed: Mar. 29, 2004

(65) Prior Publication Data

US 2005/0216990 P1 Sep. 29, 2005

(51) Int. Cl.
*A01H 5/00* (2006.01)

(52) U.S. Cl. ..... Plt./263
(58) Field of Classification Search ..... Plt./263, Plt./356
See application file for complete search history.

(56) References Cited

U.S. PATENT DOCUMENTS

| | | | |
|---|---|---|---|
| PP9,557 | P | 5/1996 | Suzuki et al. |
| PP9,754 | P | 12/1996 | Suzuki et al. |
| PP10,355 | P | 4/1998 | Murakami |

FOREIGN PATENT DOCUMENTS

| | | |
|---|---|---|
| JP | PBR 7232 | 6/1999 |
| JP | PBR 8962 | 3/2001 |

OTHER PUBLICATIONS

Germania Seed Homepage http://www.germaniaseed.com.*
Suntory Collection and Other Specialty Annuals http://www.germaniaseed.com/pdf/04–747Pineae.pdf.*
UPOV ROM GTITM Computer Database, GTI JOUVE Retrieval Software 2004/ Citation for Sunbelpisupu.*
Flower & Green Catalog 2004, Suntory Flowers, Ltd., (4 pp), Published 2003, with brief English explanation and partial translation of p. 10.
The 2004 Suntory Collection, Jackson & Perkins Wholesale, Inc., (3 pp), Published 2003, with brief English translation of last p. 7.
Pineae Peak Performers featuring the 2004 Suntory Collection, Pineae Greenhoses, Inc., (4 pp), Published 2003 with brief English translation of pp. 5 and 6.
Suntory Collection 2004, Moerheim New Plant bv, (3 pp), Published 2003 with brief English translation of p. 33.
Colour Wave Collection 2003–04, Ramm Botanicals Pty Ltd., (3 pp), Published 2002 with brief English translation of last page.

* cited by examiner

*Primary Examiner*—Kent Bell
*Assistant Examiner*—W. C. Haas
(74) *Attorney, Agent, or Firm*—Christie, Parker and Hale, LLP

(57) ABSTRACT

Disclosed herein is a new and distinct variety of *Calibrachoa* plant having a Spreading growth habit. The *Calibrachoa* plant has abundant branching, and a great profusion of blooms, the whole plant remaining in bloom for a considerable period of time. The flowers are single and small, the petals having a yellow white color with deep reddish purple vein. The inside color of the corolla throat is vivid yellow and the outside of the corolla tube is light greenish yellow with moderate reddish purple vein.

The plant exhibits high resistance to heat, cold, rain and disease.

2 Drawing Sheets

Botanical designation: *Calibrachoa* sp.
Variety denomination: 'Sunbelpisupu'.

BACKGROUND OF THE VARIETY

The present invention relates to the new variety of *Calibrachoa* plant originated from crossing of a *Calibrachoa* hybrid variety called 'Sunbelki' as the female parent and 'W12' as the male parent.

The *Calibrachoa* is a very popular plant that is used for flower bedding and potting in the summer season. There are only a few small flowered *Calibrachoa* varieties known to the inventor, such as 'SUNTORY SP-R' (U.S. Plant Pat. No. 9,557), 'Sunberubu' (U.S. Plant Pat. No. 9,754), 'Sunbelchipi' (U.S. Plant Pat. No. 10,355) and 'Sunbelki' (U.S. Plant Pat. No. 11,558), that are spreading, and have a medium plant height, with abundant branches and a high resistance to heat, rain and disease. There are even fewer varieties known to the inventors that have a great profusion of flowers, are yellowish-white with a reddish purple vein color, and have high resistance to rain, heat, and disease.

Accordingly, this invention was aimed at obtaining a new *Calibrachoa* variety having yellowish white colored with deep reddish purple vein, and very small flowers, combined with the above features.

The female parent 'Sunbelki' (U.S. Plant Pat. No. 11,558) used in the crossing of 'Sunbelpisupu' is a cultivar grown at Yokaichi-shi, Shiga-ken, Japan, having a spreading growth habit with abundant branching. It has small single flowers, the petals having a bright yellow color. The flower color of the female parent differs from that of the claimed plant.

The male parent 'W12' (unpatented) used in the crossing of 'Sunbelpisupu' is a strain of our breeding lines, having a spreading growth habit with many branches. It has small single flowers, the petals having a white color. The flower color of the male parent differs from that of the claimed plant.

In April 2000, crossing of 'Sunbelki' as the female parent and 'W12' as the male parent was conducted at Yokaichi-shi, Shiga-ken, Japan. In September 2000, 50 seedlings were obtained from that crossing. These seedlings were grown in pots in glasshouses and were evaluated from April 2001. One seedling was selected in view of its growth habit, flower size and color in September 2001. That seedling was propagated by cutting and a trial was carried out by flower potting and bedding from April to October 2002. The botanical characteristics of that plant were then examined, using similar varieties 'Sunbelki' and 'Sunbelchipi' for comparison. As a result, it was concluded that this *Calibrachoa* plant is distinguishable from any other variety, whose existence is known to us, and is uniform and stable in its characteristics. Then the new variety of *Calibrachoa* plant was named 'Sunbelpisupu'.

In the following description, the color-cording is in accordance with The R.H.S. Colour Chart.

SUMMARY OF THE VARIETY

This new variety is unlike any *Calibrachoa* commercially available, known to the inventors as evidenced by the following unique combinations of characteristics.

1. Spreading growth habit with abundant branching.
2. Having a great profusion of blooms with the entire plant remaining in bloom for a considerable period of time.
3. The flowers are single and small. The petal color is yellow white (R.H.S. 159D) with deep reddish purple (R.H.S. N78A) vein.
4. The plant has a high resistance to rain, cold, heat and disease.

The new variety 'Sunbelpisupu' differs from the similar variety 'Sunbelchipi' in the following points.

1. The leaf of 'Sunbelpisupu' is smaller than that of 'Sunbelchipi'.
2. The flower of 'Sunbelpisupu' is larger than that of 'Sunbelchipi'.
3. The petal color of 'Sunbelpisupu' is yellowish white (R.H.S. 159D) with deep reddish purple (R.H.S. N78A) vein. That of 'Sunbelchipi' is vivid purplish red (R.H.S. N57A).
4. The inside color of the corolla throat of 'Sunbelpisupu' is vivid yellow (R.H.S. 14B). That of 'Sunbelchipi' is strong yellow (R.H.S. 9A).
5. The outside color of the corolla throat of 'Sunbelpisupu' is light greenish yellow (R.H.S. 7D) with moderate reddish purple (R.H.S. 79D) vein. That of 'Sunbelchipi' is brilliant greenish yellow (R.H.S. 5C).
6. The apex shape of petal of 'Sunbelpisupu' is truncate. That of 'Sunbelchipi' is obtuse.

The new variety 'Sunbelpisupu' differs from the similar variety 'Sunbelki' in the following points.

1. The leaf of 'Sunbelpisupu' is smaller than that of 'Sunbelki'.
2. The flower of 'Sunbelpisupu' is larger than that of 'Sunbelki'.
3. The petal color of 'Sunbelpisupu' is yellowish white (R.H.S. 159D) with deep reddish purple (R.H.S. N78A) vein. That of 'Sunbelki' is bright yellow (R.H.S. 12A).
4. The inside color of the corolla throat of 'Sunbelpisupu' is vivid yellow (R.H.S. 14B). That of 'Sunbelki' is strong brown (R.H.S. 166B).
5. The outside color of the corolla throat 'Sunbelpisupu' is light greenish yellow (R.H.S. 7D) with moderate reddish purple (R.H.S. 79D) vein. That of 'Sunbelki' is greenish yellow (R.H.S. 4C) with dark reddish purple (R.H.S. 166A) vein.

This new variety of *Calibrachoa* plant, 'Sunbelpisupu', was asexually reproduced by the use of cuttings at Yokaichi-shi, Shiga-ken, Japan, and homogeneity and stability thereof were confirmed. The instant plant retains its distinctive characteristics and reproduces true to type in successive generations.

BRIEF DESCRIPTION OF THE PHOTOGRAPH

The depicted plants had been reproduced by the use of cuttings and were photographed during September 2002 while growing in typical outdoor conditions in 24 cm pots, at an age of approximately 8 months at Yokaichi-shi, Shiga-ken, Japan. The average day temperature was approximately 23° C. and the average night temperature was approximately 15° C.

DESCRIPTION OF THE VARIETY

Figure 1:
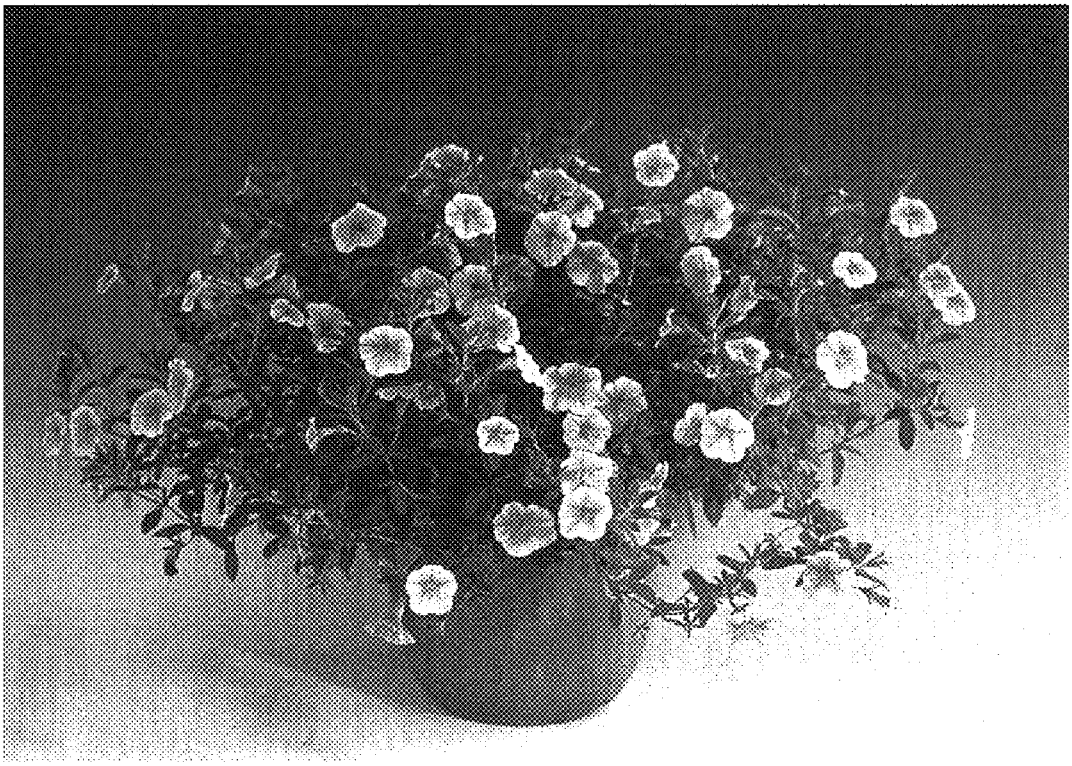
FIG. 1 illustrates a typical plant of the new variety of *Calibrachoa* plant 'Sunbelpisupu' while growing in a pot.
Figure 2:
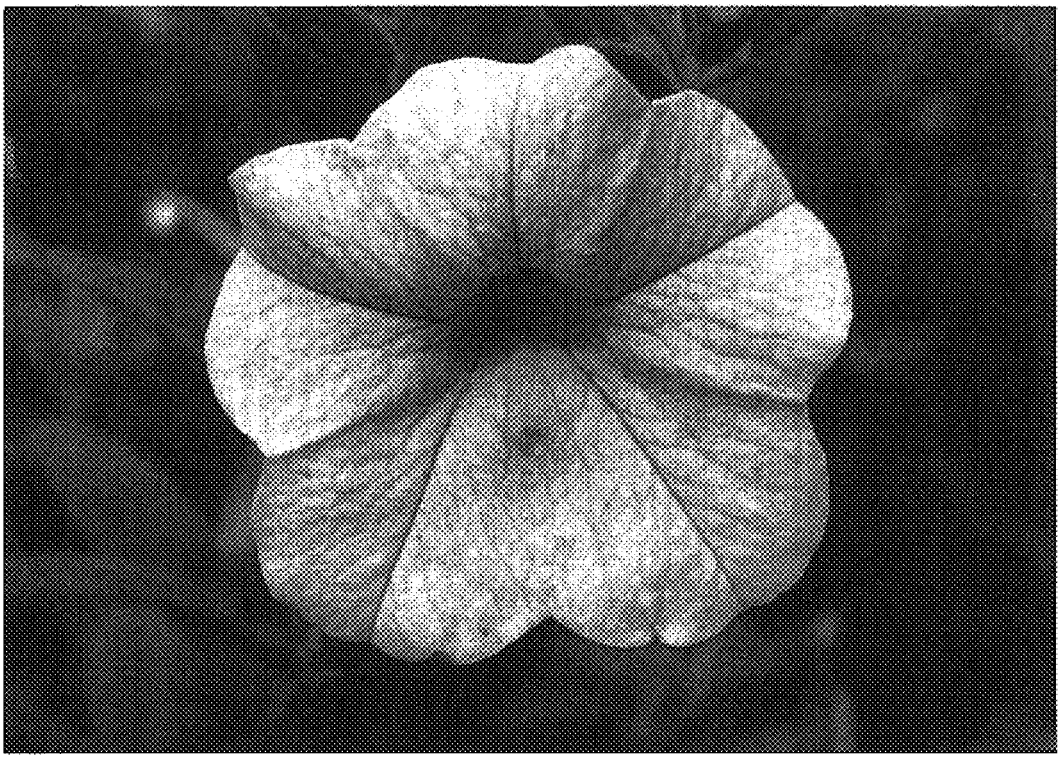
FIG. 2 illustrates a close view of typical blossoms of the new variety of *Calibrachoa* plant 'Sunbelpisupu'.

The botanical characteristics of the new and distinct variety of *Calibrachoa* plant named 'Sunbelpisupu' are as follows when observed as grown in typical outdoor conditions during December at Yokaichi-shi, Shiga-ken, Japan, at an age of approximately 11 months.

Plant:
- *Growth habit.*—Spreading.
- *Plant height.*—Approximately 21.6 cm.
- *Spreading area of plant.*—Approximately 59.0 cm.
- *Blooming period.*—Mid-April to late October in the southern Kanto area, Japan. The plant shape does not change throughout this period.

Stem:
- *Length.*—Approximately 5.0 cm.
- *Diameter.*—Approximately 1.6 mm.
- *Pubescence.*—Normal.
- *Branching.*—Approximately 50 branches per plant.
- *Internode length.*—Approximately 1.2 cm.
- *Color of stem.*—Young — R.H.S. 144B. Mature — R.H.S. 200C.

Leaf:
- *Whole shape.*—Lanceolate. The apex shape is acute, and the base shape is attenuate.
- *Length.*—Approximately 2.6 cm.
- *Width.*—Approximately 0.8 cm.
- *Color.*—Upper and lower side color is R.H.S. 144A (strong yellow green).
- *Thickness.*—Approximately 0.3 mm.
- *Pubescence.*—Present and typical of the species.

Flower:
- *Facing direction.*—Slanted upward.
- *Type.*—Single.
- *Shape.*—Funnel-shape, with five-fissured limb.
- *Shape of petal tip.*—Truncate.
- *Lobation.*—Shallow.
- *Waving of petal.*—Weak.
- *Diameter.*—Approximately 3.2 cm.
- *Color.*—Petal; Upper surface, near R.H.S. 159D (yellow white) with R.H.S. N78A (deep reddish purple) midvein. Lower surface, near R.H.S. 78A. Inside color of the corolla throat is vivid yellow (R.H.S. 14B). Outside color of the corolla throat is light greenish yellow (R.H.S. 7D) with moderate reddish purple (R.H.S. 79D) vein.

*Reproductive organs.*—1 normal pistil and 5 normal stamens. The stigma is club-shaped and R.H.S. N144D (light yellow green) in coloration. The style is approximately 8 mm in length and R.H.S. 145B (brilliant yellow green) in coloration. The ovary is R.H.S. N144D (light yellow green) in coloration. The stamens commonly are of variable length from approximately 4.0 to 1.0 mm. Pollen is formed in a quantity that is typical of *Calibrachoa* and is near R.H.S. 21A (vivid orange yellow) in coloration.

*Fertility.*—Fertile, but self-incompatible.

*Peduncle.*—Approximately 0.5 mm in diameter and approximately 1.1 cm in length. The texture is smooth. The color is near R.H.S. 144B.

*Calyx.*—Narrow. 5 sepals in fused at the base.

*Diameter.*—Approximately 15 mm.

*Depth.*—Approximately 13 mm.

*Color* (*both surfaces*).—Near R.H.S. 144A.

*Texture* (*both surfaces*)—Smooth.

*Seeds.*—R.H.S. N186A (strong red) in coloration, approximately 0.6 mm in diameter, and generally round. The quantity is typical of *Calibrachoa.*

Physiological and ecological characteristics: High resistance to cold, heat, rain and disease, such as Powdery mildew. The resistance to heat and rain is very strong. Low temperature tolerance is at least 5° C.; high temperature tolerance is approximately 35° C.

This new variety of *Calibrachoa* plant is most suitable for flower bedding and potting, particularly in hanging pots or planters. Pinching of old blossoms will enhance the formation of new blossoms.

It is claimed:

1. A new and distinct variety of *Calibrachoa* plant named 'Sunbelpisupu', substantially as herein illustrated and described.

* * * * *